United States Patent
Sullivan

(10) Patent No.: US 11,717,687 B2
(45) Date of Patent: Aug. 8, 2023

(54) ASYSTOLE AND COMPLETE HEART BLOCK DETECTION

(71) Applicant: West Affum Holdings Corp., Grand Cayman (KY)

(72) Inventor: Joseph L. Sullivan, Kirkland, WA (US)

(73) Assignee: West Affum Holdings DAC, Dublin (IE)

( * ) Notice: Subject to any disclaimer, the term of this patent is extended or adjusted under 35 U.S.C. 154(b) by 211 days.

(21) Appl. No.: 17/142,477

(22) Filed: Jan. 6, 2021

(65) Prior Publication Data

US 2021/0205618 A1   Jul. 8, 2021

Related U.S. Application Data

(60) Provisional application No. 62/957,411, filed on Jan. 6, 2020.

(51) Int. Cl.
*A61N 1/365* (2006.01)
*A61N 1/362* (2006.01)
(Continued)

(52) U.S. Cl.
CPC ............. *A61N 1/365* (2013.01); *A61B 5/352* (2021.01); *A61N 1/3625* (2013.01); *A61N 1/3904* (2017.08)

(58) Field of Classification Search
CPC .... A61N 1/365; A61N 1/3625; A61N 1/3904; A61B 5/352; A61B 5/333; A61B 5/353; A61B 5/363; A61B 5/366; A61B 5/33
See application file for complete search history.

(56) References Cited

U.S. PATENT DOCUMENTS

| 3,724,355 A | 4/1973 | Busch et al. |
| 3,724,455 A | 4/1973 | Unger |

(Continued)

FOREIGN PATENT DOCUMENTS

WO   9839061 A2   9/1998

OTHER PUBLICATIONS

Kirstein et al., "A CMOS-based Tactile Sensor for Continuous Blood Pressure Monitoring" Proceeding of the Design, Automation and Test in Europe Conference and Exhibition, IEEE Computer Society, Oct. 24, 2007.

(Continued)

*Primary Examiner* — Catherine M Voorhees
(74) *Attorney, Agent, or Firm* — Spectrum IP Law Group LLC

(57) ABSTRACT

In one example, an apparatus of a wearable cardioverter defibrillator (WCD) system comprises a support structure wearable by a patient, a plurality of electrocardiogram (ECG) electrodes to obtain an ECG signal, a processor to receive and analyze the ECG signal of the patient, wherein the processor is configured to monitor four or more channels of the ECG signal, a high voltage subsystem coupled with defibrillation electrodes configured to be coupled with patient, wherein the processor is configured to cause the high voltage subsystem to apply a therapeutic shock to the patient through the defibrillation electrodes in response to a shockable event detected by the processor from the ECG signal. The processor measures a peak-to-peak amplitude of QRS complexes of the ECG signal, and detects asystole in the patient when the peak-to-peak amplitude of one or more QRS complexes is less than an asystole threshold. Other examples and related methods are disclosed herein.

18 Claims, 11 Drawing Sheets

(51) Int. Cl.
  *A61B 5/352* (2021.01)
  *A61N 1/39* (2006.01)

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,474,574 A | 12/1995 | Payne et al. |
| 5,662,690 A | 9/1997 | Cole et al. |
| 5,782,878 A | 7/1998 | Morgan et al. |
| 5,792,204 A | 8/1998 | Snell |
| 5,895,298 A * | 4/1999 | Faupel ............... A61B 5/30 439/729 |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,773 B1 * | 10/2001 | Taylor .............. A61N 1/3904 600/518 |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 10,016,614 B2 * | 7/2018 | Sullivan ............... A61B 5/0205 |
| 2011/0022105 A9 | 1/2003 | Owen et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2008/0033495 A1 | 2/2008 | Kumar |
| 2008/0312709 A1 | 12/2008 | Volpe et al. |
| 2009/0005827 A1 | 1/2009 | Weintraub et al. |
| 2010/0007413 A1 | 1/2010 | Herleikson et al. |
| 2010/0298899 A1 | 11/2010 | Donnelly et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0088660 A1 | 3/2014 | Debardi et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0045156 A1 | 2/2016 | Kaib et al. |
| 2016/0082277 A1 | 3/2016 | Foshee, Jr. et al. |
| 2017/0056682 A1 | 3/2017 | Kumar et al. |
| 2017/0128735 A1 | 5/2017 | Gustavson et al. |
| 2018/0110995 A1 | 4/2018 | Sullivan et al. |
| 2018/0117299 A1 | 5/2018 | Gustavson et al. |
| 2018/0185662 A1 | 7/2018 | Foshee, Jr. et al. |
| 2019/0380610 A1 * | 12/2019 | Bornzin ............... A61B 5/316 |
| 2021/0100457 A1 | 4/2021 | Sullivan |
| 2021/0338168 A1 * | 11/2021 | Landman ............ A61B 5/7221 |

OTHER PUBLICATIONS

Heartstart MRx and XL AED Algorithm—Application Note, Jul. 2001, Edition 2 Philips Healthcare, USA.

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

* cited by examiner

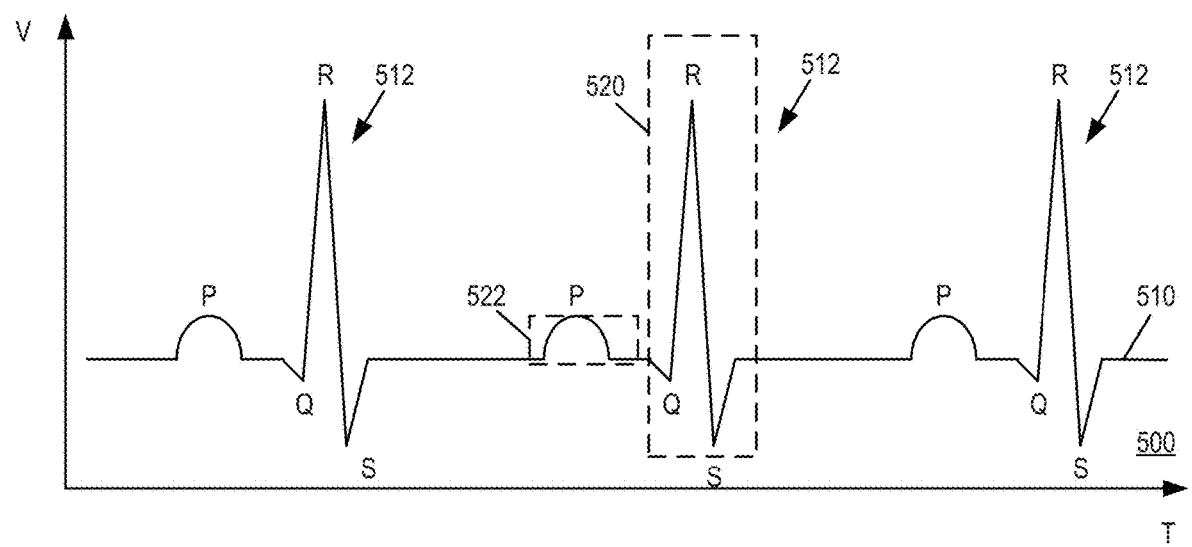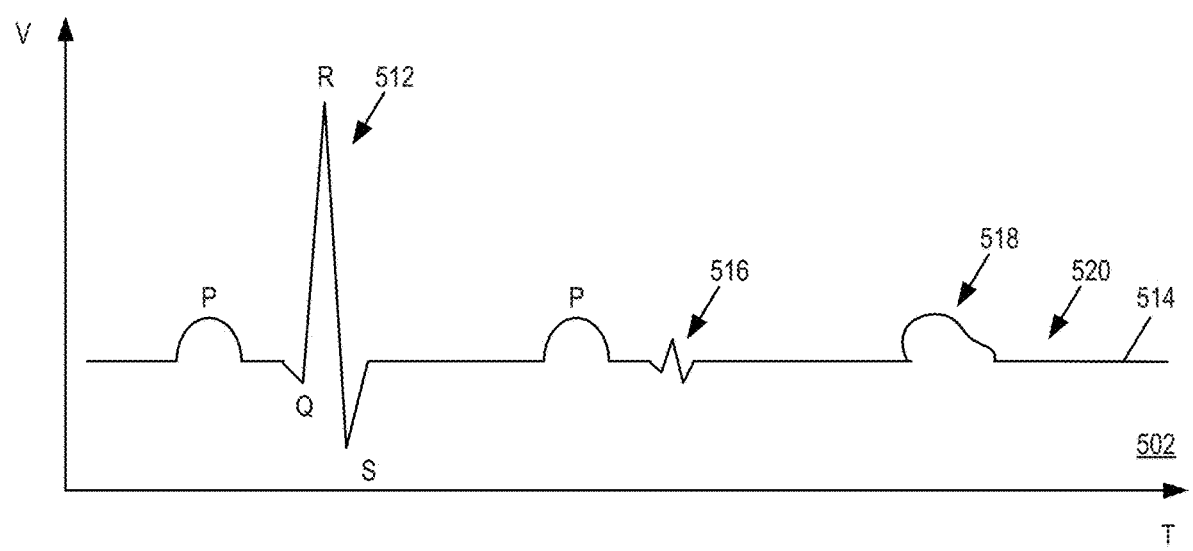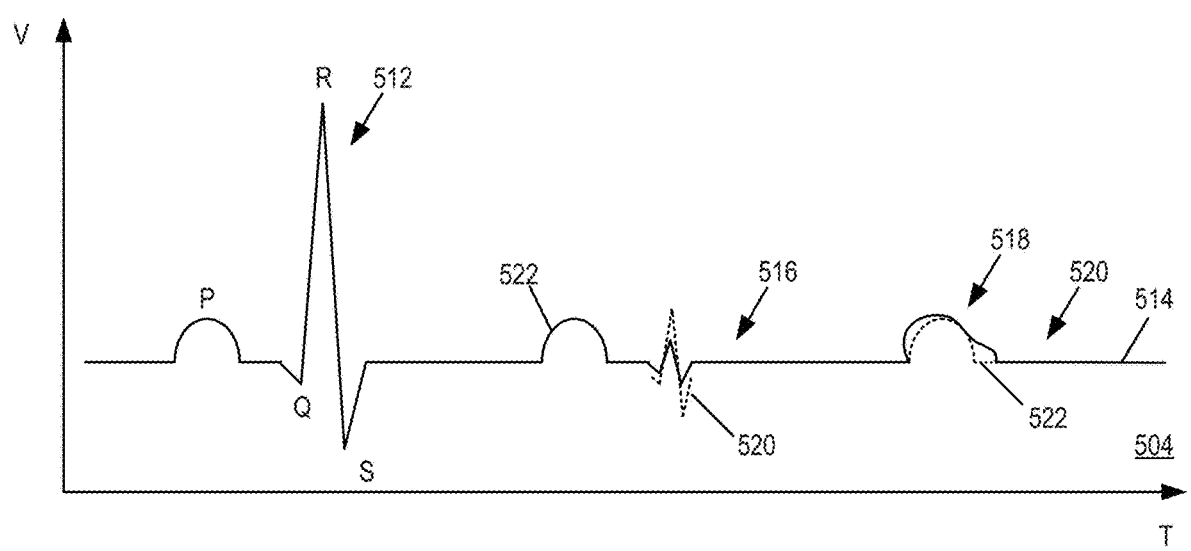
FIG. 5

ASYSTOLE AND COMPLETE HEART BLOCK DETECTION

CROSS-REFERENCE TO RELATED APPLICATIONS

The present application claims the benefit of U.S. Provisional Application No. 62/957,411 filed Jan. 6, 2020. Said Application No. 62/957,411 is hereby incorporated herein by reference in its entirety.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, for example within 10 minutes, unless treated in the interim.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

As a further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear. The WCD system further includes electronic components, such as a defibrillator and electrodes, coupled to the harness, vest, or other garment. When the patient wears the WCD system, the electrodes may make good electrical contact with the patient's skin, and therefore can help sense the patient's ECG. If a shockable heart arrhythmia is detected from the ECG, then the defibrillator delivers an appropriate electric shock through the patient's body, and thus through the heart. This may restart the patient's heart and thus save their life.

WCD systems analyze the patient's ECG data as part of the determination whether to apply a therapeutic electric shock to the patient. WCDs are designed to detect and treat VT/VF, but they also may encounter patients with extreme bradycardia and asystole. Current WCDs alarm and call for help when they encounter these rhythms but generally have no ability to treat those conditions. Furthermore, current WCDs generally are not capable of distinguishing bradycardia and asystole from other conditions.

DESCRIPTION OF THE DRAWING FIGURES

Claimed subject matter is particularly pointed out and distinctly claimed in the concluding portion of the specification. However, such subject matter may be understood by reference to the following detailed description when read with the accompanying drawings in which:

FIG. 5 is a diagram of ECG signals illustrating P-waves in addition to QRS complexes wherein P-wave morphologies are accounted for in detected asystole in accordance with one or more embodiments.

Figure 1:
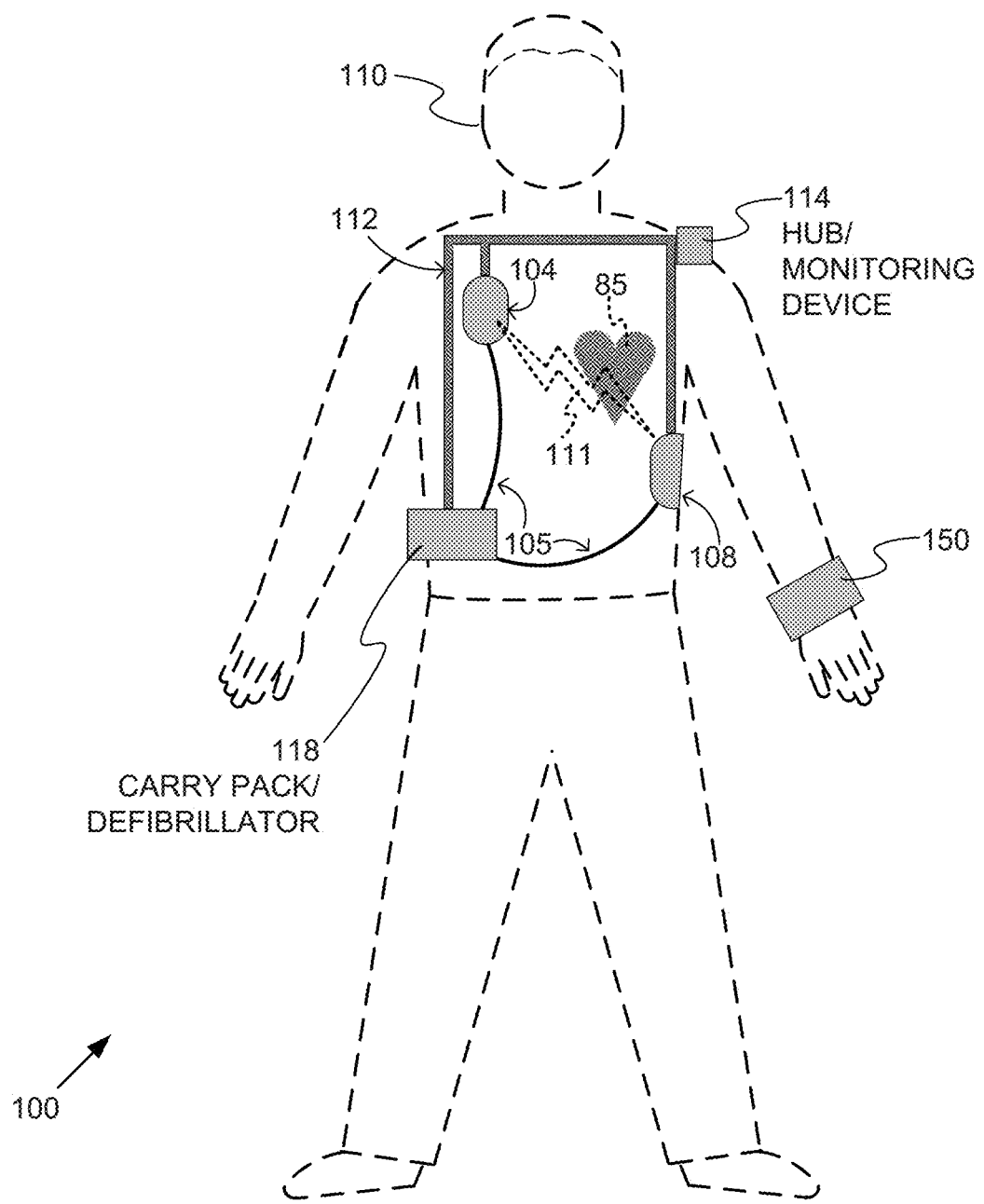
FIG. 1 is a diagram of components of an example wearable cardioverter defibrillator (WCD) system in accordance with one or more embodiments.

It will be appreciated that for simplicity and/or clarity of illustration, elements illustrated in the figures have not necessarily been drawn to scale. For example, the dimensions of some of the elements may be exaggerated relative to other elements for clarity. Further, if considered appropriate, reference numerals have been repeated among the figures to indicate corresponding and/or analogous elements.

DETAILED DESCRIPTION

In the following detailed description, numerous specific details are set forth to provide a thorough understanding of claimed subject matter. It will, however, be understood by those skilled in the art that claimed subject matter may be practiced without these specific details. In other instances, well-known methods, procedures, components and/or circuits have not been described in detail.

In the following description and/or claims, the terms coupled and/or connected, along with their derivatives, may be used. In particular embodiments, connected may be used to indicate that two or more elements are in direct physical and/or electrical contact with each other. Coupled may mean that two or more elements are in direct physical and/or electrical contact. Coupled, however, may also mean that two or more elements may not be in direct contact with each other, but yet may still cooperate and/or interact with each other. For example, "coupled" may mean that two or more elements do not contact each other but are indirectly joined together via another element or intermediate elements. Finally, the terms "on," "overlying," and "over" may be used in the following description and claims. "On," "overlying," and "over" may be used to indicate that two or more elements are in direct physical contact with each other. It should be noted, however, that "over" may also mean that two or more elements are not in direct contact with each other. For example, "over" may mean that one element is above another element but not contact each other and may have another element or elements in between the two elements. Furthermore, the term "and/or" may mean "and", it may mean "or", it may mean "exclusive-or", it may mean "one", it may mean "some, but not all", it may mean "neither", and/or it may mean "both", although the scope of claimed subject matter is not limited in this respect. In the following description and/or claims, the terms "comprise" and "include," along with their derivatives, may be used and are intended as synonyms for each other.

Referring now to FIG. 1, a diagram of components of an example wearable cardioverter defibrillator (WCD) system in accordance with one or more embodiments will be discussed. A wearable cardioverter defibrillator (WCD) system 100 according to embodiments may protect an ambulatory patient 110 by electrically restarting his or her heart if needed. Such a WCD system 100 may have a number of components. These components can be provided separately as modules that can be interconnected, or can be combined with other components, and so on.

FIG. 1 depicts a patient 110. Patient 110 may also be referred to as a person and/or wearer since the patient is wearing components of the WCD system 100. Patient 110 is ambulatory, which means that, while wearing the wearable portion of the WCD system 100, patient 110 can walk around and is not necessarily bed-ridden. While patient 110 also can be considered a "user" of the WCD system 100, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The context of these and other related terms within this description should be interpreted accordingly.

A WCD system 100 according to embodiments can be configured to defibrillate the patient 110 who is wearing the designated parts the WCD system 100. Defibrillating can be by the WCD system 100 delivering an electrical charge to the patient's body in the form of an electric shock. The electric shock can be delivered in one or more pulses.

FIG. 1 also depicts components of a WCD system 100 made according to embodiments. One such component is a support structure 112, or garment, that is wearable by ambulatory patient 110. Accordingly, support structure 112 is configured to be worn by ambulatory patient 110 for at least several hours per day, and for at least several days, even a few months. It will be understood that support structure 112 is shown only generically in FIG. 1, and in fact partly conceptually. FIG. 1 is provided merely to illustrate concepts about support structure 112, and is not to be construed as limiting how support structure 112 is implemented, or how it is worn.

Support structure 112 can be implemented in many ways. For example, it can be implemented in a single component or a combination of multiple components. In embodiments, support structure 112 can include a vest, a half-vest, a garment, and so on. In such embodiments such items can be worn similarly to analogous articles of clothing. In embodiments, support structure 112 can include a harness, one or more belts or straps, and so on. In such embodiments, such items can be worn by the patient around the torso, hips, over the shoulder, and so on. In embodiments, support structure 112 can include a container or housing, which optionally can be waterproof. In such embodiments, the support structure 112 can be worn by being attached to the patient's body by adhesive material, for example as shown and described in U.S. Pat. No. 8,024,037 which is incorporated herein by reference in its entirety. Support structure 112 can be implemented as described for the support structure of U.S. application Ser. No. 15/120,655, published as US 2017/0056682 A1, which is incorporated herein by reference in its entirety. In such embodiments, the person skilled in the art will recognize that additional components of the WCD system 100 can be in the housing of a support structure instead of being attached externally to the support structure, for example as described in the US 2017/0056682 A1 document. There can be other examples.

FIG. 1 shows a sample external defibrillator 118. In some embodiments, external defibrillator may be referred to as a carry pack since the components of external defibrillator can be contained in an external package that is carried by the patient 110, for example using a shoulder strap. As described in more detail later in this document, some aspects of external defibrillator 118 include a housing and an energy storage module within the housing. As such, in the context of a WCD system 100, defibrillator 118 is sometimes called a main electronics module. The energy storage module can be configured to store an electrical charge. Other components can cause at least some of the stored electrical charge to be discharged via electrodes through the patient to deliver one or more defibrillation shocks through the patient 110.

FIG. 1 also shows sample defibrillation electrodes 104 and 108, which are coupled to external defibrillator 100 via electrode leads 105. Defibrillation electrodes 104 and 108 can be configured to be worn by patient 110 in several ways. For instance, defibrillator 100 and defibrillation electrodes 104 and 108 can be coupled to support structure 112, directly or indirectly. In other words, support structure 112 can be configured to be worn by an ambulatory patient 110 to maintain at least one of electrodes 104 or 108 on the body of ambulatory patient 110, while patient 110 is moving around, and so on. The electrode can be thus maintained on the body by being attached to the skin of patient 110, simply pressed against the skin directly or through garments, etc. In some embodiments the electrode is not necessarily pressed against the skin, but becomes biased that way upon sensing a condition that could merit intervention by the WCD system 100. In addition, many of the components of defibrillator 118 can be considered coupled to support structure 112 directly, or indirectly via at least one of defibrillation electrodes 104 and/or 108.

When defibrillation electrodes 104 and 108 make good electrical contact with the body of patient 110, defibrillator 118 can administer, via electrodes 104 and 108, a brief, strong electric pulse 111 through the body. Pulse 111 is also known as shock, defibrillation shock, therapy, electrotherapy, therapy shock, etc. Pulse 111 is intended to go through and restart heart 85 to save the life of patient 110. Pulse 111 can further include one or more pacing pulses of lesser magnitude to simply pace heart 85 if needed, and so on.

A typical defibrillator can decide whether to defibrillate based on an electrocardiogram (ECG) signal of the patient. External defibrillator 118, however, may initiate defibrillation, or hold-off defibrillation, based on a variety of inputs, with the ECG signal merely being one of these inputs.

A WCD system 100 according to embodiments can obtain data from patient 110. For collecting such data, the WCD system 100 may optionally include a hub or monitoring device 114. Device 114 is can be provided as a standalone device, for example not within the housing of defibrillator 118. Device 114 can be configured to sense or monitor at least one local parameter. A local parameter can be a parameter of patient 110, or a parameter of the WCD system 100, or a parameter of the environment, as will be described later in this document. In some embodiments, monitoring device 114 can comprise or be referred to as a hub or similar device through which connections and/or leads may be made of the various components of the WCD system 100. For example, at least some of the leads of external defibrillator 118 may be connected to and/or routed through the monitoring device 114 including, for example, one or more ECG leads, a right-leg drive (RLD) lead, leads connected to the defibrillation electrodes 104 and/or 108, and so on. In some embodiments, monitoring device 114 can include a controller or processor that is used to implement at least a portion of the shock/no-shock algorithm to determine whether a shock should or should not be applied to the patient 110, although the scope of the disclosed subject matter is not limited in this respect.

For some of these parameters, device 114 can include one or more sensors or transducers. Each one of such sensors can be configured to sense a parameter of patient 110, and to render an input responsive to the sensed parameter. In some embodiments the input is quantitative, such as values of a sensed parameter. In other embodiments the input is qualitative, such as informing whether a threshold is crossed, and so on. Sometimes these inputs about patient 110 are also called physiological inputs or patient inputs. In embodiments, a sensor can be construed more broadly, as encompassing many individual sensors.

Optionally, device 114 can be physically coupled to support structure 112. In addition, device 114 may be communicatively coupled with other components that are coupled to support structure 112. Such communication can be implemented by a communication module, as will be deemed applicable by a person skilled in the art in view of this description.

In embodiments, one or more of the components of the shown WCD system 100 may be customized for patient 110. This customization may include several aspects. For instance, support structure 112 can be fitted to the body of patient 110. For another instance, baseline physiological parameters of patient 110 can be measured, such as the heart rate of patient 110 while resting, while walking, motion detector outputs while walking, etc. The measured values of such baseline physiological parameters can be used to customize the WCD system 100 to make its diagnoses more accurate, since patients' bodies differ from one another. Of course, such parameter values can be stored in a memory of the WCD system 100, and so on. Moreover, a programming interface can be made according to embodiments, which receives such measured values of baseline physiological parameters. Such a programming interface may input automatically in the WCD system 100 these values along with other data In one or more embodiments, WCD system 100 can include an external monitor 150 that is capable of monitoring various physiological parameters of the patient. For example, external monitor 150 can comprise a non-invasive blood pressure (NIBP) monitor to measure the blood pressure of the patient 110 as one or more of the patient parameters collected by WCD system 100. In another example, external monitor 150 can comprise a pulse oximeter to measure the oxygen saturation of the patient 110. In yet another example, external monitor 150 can measure the heart rate of the patient 110 independent from the ECG signal obtained by hub/monitoring device 114. Monitoring device 150 can be configured to combine multiple functions to take multiple types of physiological parameter measurements of the patient 110, and the scope of the disclosed subject matter is not limited in these respects. Furthermore, external monitor 150 can obtain frequent measurements of one or more physiological parameters while the patient 110 is wearing the monitor through the day and/or during the night when the patient 110 is sleeping.

The external monitor 150 can be provided in various types of form factors to be placed on the patient's body at various locations and/or to integrate with WCD system 100 in various ways. For example, in some embodiments, external monitor 150 may be worn on the wrist of the patient 110 or various other locations on the patient 110 such as on the arm, leg, ankle, chest, or back of the patient 110 depending on the provided form factor and/or technology utilized by the external monitor 150 to obtain a physiological parameter reading.

In some embodiments, external monitor 150 may be incorporated into an external device or accessory such as a smartphone that employ various sensors. Such devices may come in various other form factors such as a patch, watch, earring, eyeglasses, ankle bracelet, and so on, wherein the external monitor 150 can be unobtrusive and in location in which the patient's vasculature may be near the skin so that an optical sensor of external monitor 150 can obtain good readings.

In some embodiments, external monitor 150 can include a sensor built into the alert button or stop button 120 (see FIG. 2) of the WCD system 100 wherein the alert button or stop button 120 is used by the patient 110 to stop an impending shock if the patient so desires. In such embodiments, the patient 110 is already aware of the location of the alert button or stop button 120 which would provide a simple and readily available device for the patient to use to take a measurement such as blood pressure and/or heart rate. In addition, when the external monitor 150 is in the alert button or stop button 120, the patient's blood pressure and/or heart rate can be obtained whenever the patient 110 needs to abort a shock.

As previously mention, in one or more embodiments, the external monitor 150 can include or otherwise comprise an optical pulse oximetry sensor and/or a methemoglobin sensor. In other embodiments, external monitor 150 can be incorporated in one or more of the ECG electrodes of the WCD system 100. Such a sensor can be an optical sensor as described above, or an electro-mechanical sensor such as described in "*A CMOS-based Tactile Sensor for Continuous Blood Pressure Monitoring*", Kirstein, Sedivy, et al., Proceedings of the Design, Automation and Test in Europe Conference and Exhibition, 1530-1591/05 (March 2005) which is incorporated herein by reference in its entirety.

In other embodiments, the external monitor 150 can be adapted for use in proposed adhesive type defibrillators as disclosed in U.S. Pat. No. 8,024,037. For example, the external monitor 150 can be disposed in one of the adhesive modules as shown in the '037 patent, or in an "appendage" or "flap" that extends from the module so that the external monitor 150 is positioned on an appropriate location on the patient. Embodiments of a cuff-less NIBP sensor can include a wireless communication interface such as BLUETOOTH, near-field communication (NFC), Wi-Fi DIRECT, ZIGBEE, and so on, to transmit the blood pressure data to a module of the WCD system 100, to a personal communication device of the WCD system 100 for example as disclosed in U.S. Pat. No. 8,838,235, or to another remote device. Said U.S. Pat. No. 8,838,235 is incorporated herein by reference in its entirety. In some embodiments, a wired communication link can be used instead of a wireless communication link. For example, the external monitor 150 can be implemented in an electrode that can be configured so that the physiological parameter data is transmitted on a wire bundled with the wire or wires of the electrode sensors, or multiplexed on the same wire as the electrode data, and so on.

Figure 2:
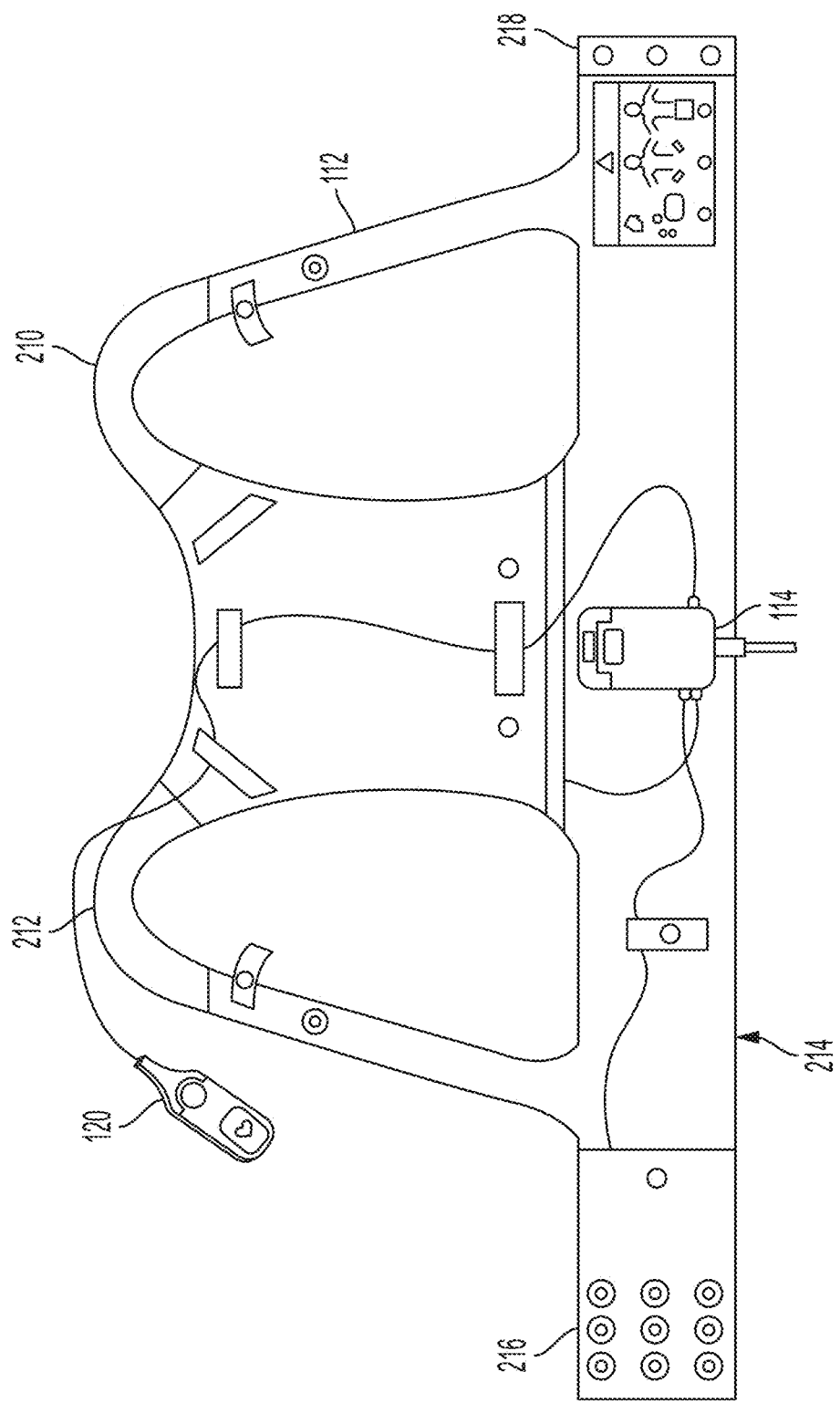
FIG. 2 is a diagram of a back view of a garment of a WCD in accordance with one or more embodiments.

Referring now to FIG. 2, a diagram of a back view of a garment of a WCD in accordance with one or more embodiments will be discussed. The garment shown in FIG. 2 can comprise the support structure 112 of FIG. 1 and is shown in a vest configuration. The garment can include shoulder straps 210 and 212 to be placed over the shoulders of the patient 110 and for support of the support structure 112. The garment may include a belt portion 214 to be fastened around the waist of the patient 110. The belt portion 214 may include various fasteners 216 and 218, for example closure snaps, to allow the garment to be fitted to different sized users. Hub/monitoring device 114 can be attached to the back side of the garment, for example on or near the belt portion 214, to allow various cables to be connected to hub 114 including alert button (or divert button or stop button) 120 and cabling to connect to the therapy/defibrillator electrodes and ECG electrodes (not shown). In some embodiments, support structure 112 can comprise a vest-like fabric garment to be worn on the patient's body underneath an outer shirt or other clothing to allow the electrodes to contact the patient's skin and hold the electrodes near and/or in direct contact with the patient's skin. Such an arrangement allows for the WCD system 100 to obtain ECG signals from the patient 110 and to allow the shock 111 to be applied to the patient 110 when appropriate.

Figure 3:
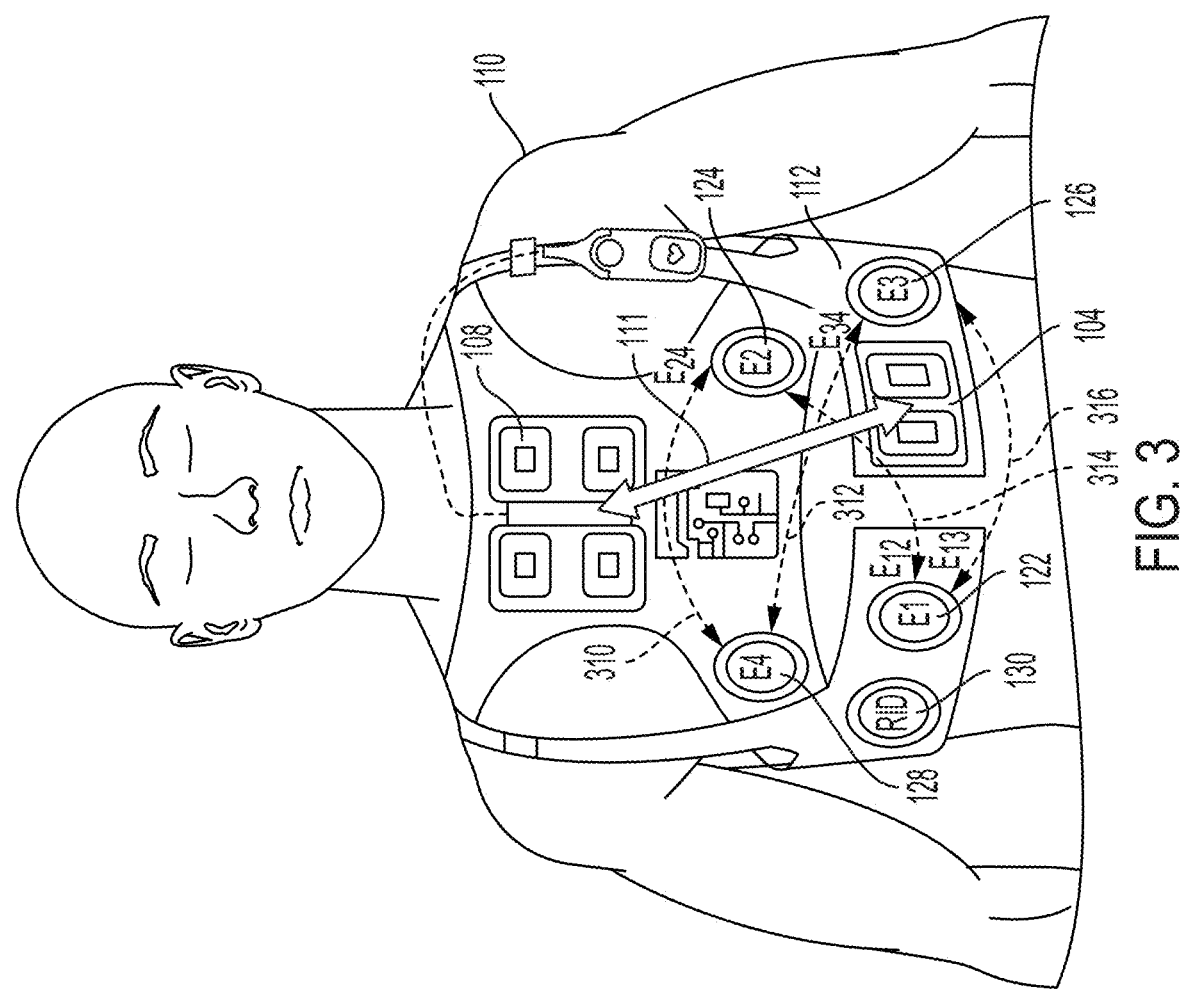
FIG. 3 is a diagram illustrating four ECG monitoring vectors used in a WCD in accordance with one or more embodiments.

Referring now to FIG. 3, a diagram illustrating four ECG monitoring vectors used in a WCD in accordance with one or more embodiments will be discussed. As shown in FIG. 3, patient 110 can wear support structure 112 that can include ECG electrodes such as electrode (E1) 122, electrode (E2) 124, electrode (E3) 126, and electrode (E4) 128 at various locations around the patient's torso to obtain ECG signals from the patient 110. Support structure 112 can also include a right leg drive (RLD) electrode 130 as a reference for differential signals. In some embodiments, the ECG signals obtained by WCD system 100 can be digitized, and the digitized ECG signals can be referenced to an isolated ground of the ECG front end circuitry. Differential vectors can be formed by subtracting two digitized ECG signals. ECG rhythm analysis then can be performed on these four vectors. Such differential vectors may include, for example, vector (E24) 310, vector (E34) 312, vector (E12) 214, and vector (E13) 216. The defibrillator shock 111 may be generated between the anterior defibrillation pad 104 and the posterior defibrillation pad 108. The ECG analysis algorithm includes provisions for excluding vectors that have noise or when a leads-off condition or situation is detected. Monitoring four vectors rather than monitoring two vectors is believed to contribute to enhanced ECG signal analysis and processing of the shock application algorithm to reduce the number of false shock events.

In some embodiments, the signals from four ECG electrodes can be combined to form up to six different vectors. In some embodiments, WCD 100 uses four vectors for QRS complex analysis and/or heart rate analysis to determine if a shock should be applied. The WCD 100 is also capable of performing the analysis and shock application determination if one or more of the vectors is noisy or one or more of the ECG leads is in a lead-off condition wherein the lead is not contacting the patient's skin or is not sufficiently contacting the patient's skin to allow an ECG signal to be obtained with that ECG lead. In some embodiments, three ECG electrodes may be used and three ECG vectors may be analyzed. In other embodiments, five or six ECG vectors may be analyzed using four ECG electrodes. In some embodiments, a single vector is used and analyzed. It should be noted that in general WCD system 100 may use and analyze fewer than four vectors or greater than four vectors, and the number of vectors can be increased beyond six vectors by using additional ECG electrodes, and the scope of the disclosed subject matter is not limited in this respect.

In one or more embodiments as shown in FIG. 3, the ECG electrodes can be placed circumferentially around the torso of the patient 110 so that the garment or support structure 112 can be used to ensure adequate electrode-skin contact with the patient's skin. It should be noted that other alternative electrode placements may be used, and the scope of the disclosed subject matter is not limited in this respect. For example, adhesive electrode embodiments can provide flexibility in electrode placement in selected locations of the patient's body and may achieve better signal pickup at these selected locations. For example, electrode locations can be selected during a patient-fitting process in which various electrode locations can be changed, and those locations with better or the best ECG signals can be selected, although the scope of the disclosed subject matter is not limited in this respect.

In one or more embodiments, WCD system 100 can be configured to detect asystole and non-perfusing bradycardia in patient 110. The WCD system 100 can be configured to non-invasively detect asystole and/or non-perfusing bradycardia. In some embodiments, WCD system 100 cab be configured to provide external pacing as a therapy for detected asystole and/or non-perfusing bradycardia. In some embodiments, asystole can be detected simply by the absence of QRS complexes which is a flatline ECG (see FIG. 4 below). In some embodiments, WCD system 100 can be configured to analyze ECG signals on multiple vectors to confirm that QRS complexes are not present on any of the available vectors. The WCD system 100 may check vectors that are not normally used before rendering an asystole decision. If the patient is in asystole, all vectors should have a flatline ECG. In some embodiments, the WCD system 100 can be configured to detect whether the ECG leads that have an electrode off or discernable noise, and in response to such detection can exclude the signals from those ECG leads from consideration for asystole detection.

In accordance with one or more embodiments, asystole can be detected with greater certainty by analyzing more than two vectors. WCD system 100 can utilize four ECG electrodes to generate up to six ECG vectors. If all vectors are analyzed, then there is less chance that a low-amplitude rhythm may be mistaken for asystole.

FIG. 3 shows the relationship between physical electrode placement and ECG vectors for an example WCD embodiment. The ECG electrode (E1) 122, electrode (E2) 124, electrode (E3) 126, and electrode (E4) comprise single-ended monitored electrodes. In some embodiments the right leg drive (RLD) electrode 130 can be used to manage common mode noise. Vector (E24) 310, vector (E34) 312, vector (E12) 314, and vector (E13) 316 are the differential vectors that are derived from the single-ended vectors. Embodiment of how the ECG signals and vectors obtained with WCD system 100 can be used to detect asystole and non-perfusing bradycardia are discussed below.

Figure 4:
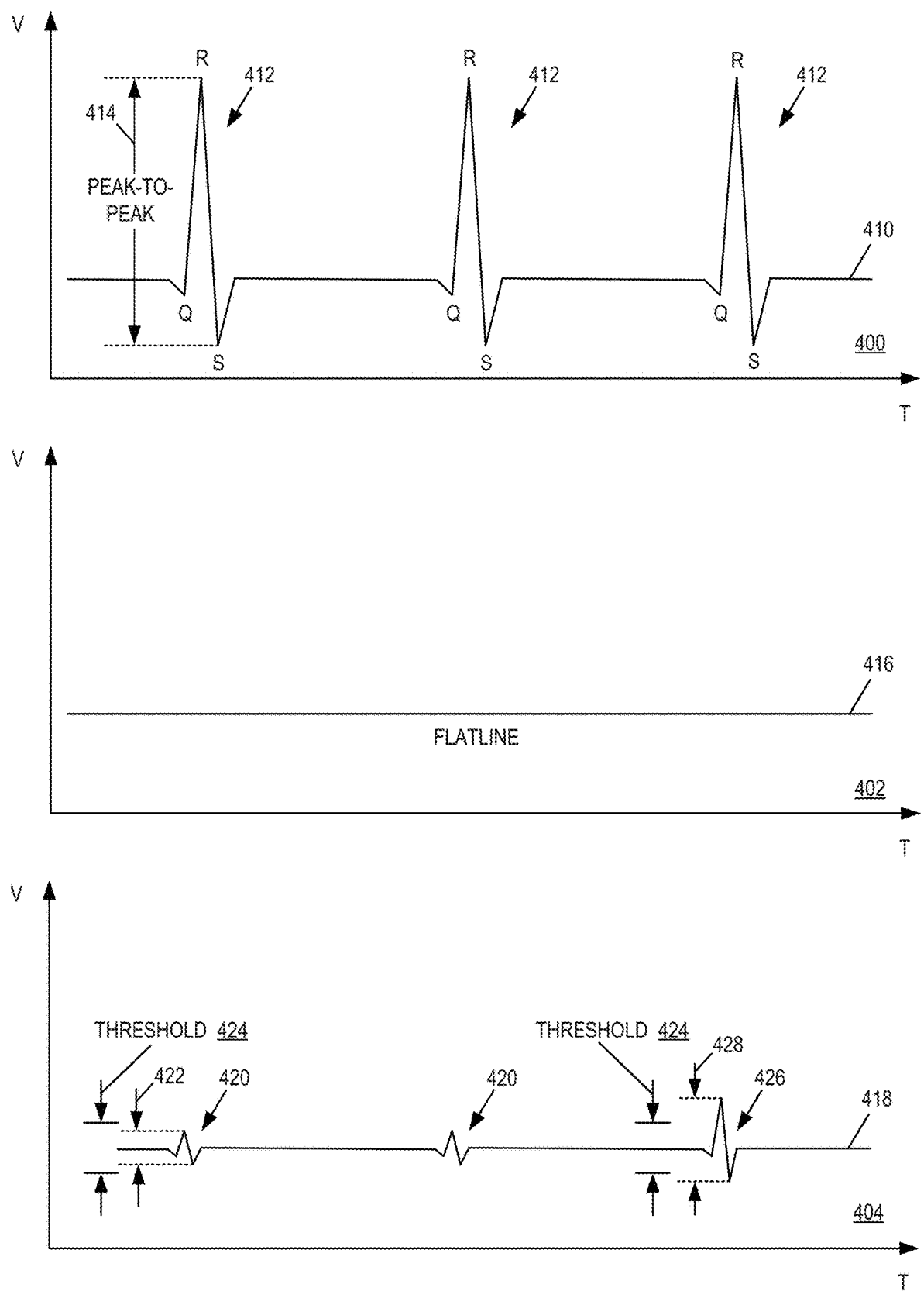
FIG. 4 is a diagram of ECG signals illustrating an asystole threshold based on peak-to-peak values of the detected QRS complexes in accordance with one or more embodiments.

Referring now to FIG. 4, a diagram of ECG signals illustrating an asystole threshold based on peak-to-peak values of the detected QRS complexes in accordance with one or more embodiments will be discussed. Asystole can refer to the absence of ventricular contractions due to total cessation of electrical activity in the heart such that the heart does not contract. When there is no heart contraction, there is no blood flow in the patient 110. The patient's ECG signal will be a complete flatline. Sometimes it can be difficult to distinguish between asystole and fine ventricular fibrillation (VF) which refers to a chaotic heart rhythms having very small amplitudes. In one or more embodiments, an amplitude threshold can be used to separate fine VF from asystole. For example, if the peak-peak value of an ECG signal is greater than 100 microvolts (μV) then it can be classified as fine VF while a signal less than 100 μV would be classified as asystole. It should be noted that fine VF can be a shockable condition whereas asystole would not be treated with a shock. As a result, WCD 100 can be configured to distinguish between fine VF with low-amplitude QRS complexes and asystole with no QRS complexes.

Plot 400 illustrates voltage versus time of a normal ECG signal 410. QRS complexes 412 are shown in ECG signal 410 but p-waves and t-waves are omitted for purposes of example. A normal QRS complex 412 can have a peak-to-peak value 414 of up to about 2.5 millivolts (mV) or 3.0 mV. In contrast to the normal ECG signal 410 shown in plot 400, plot 402 shows an ECG signal 416 having no QRS complexes and therefore there is no peak-to-peak signal 414. Such an ECG signal 416 can be referred to as a flatline which indicates asystole.

Plot 404 shows an ECG signal 418 with QRS complexes 420 having low peak-to-peak values 414. Such low-amplitude QRS complexes 420 can be difficult to distinguish from asystole. In one or more embodiments, an amplitude threshold 424 can be used to distinguish between low-amplitude QRS complexes and asystole. The threshold can be for example about 100 μV, although the scope of the disclosed subject matter is not limited in this respect. As can be seen in plot 404, the peak-to-peak amplitude 422 of QRS complexes 420 is less than the threshold 424. As a result, these QRS complexes 420 can be classified as asystole. The peak-to-peak amplitude 428 of QRS complex 426 is greater than the threshold 424. As a result, QRS complex 426 can be classified as fine VF.

WCD system 1000 can also utilize other techniques to avoid unnecessary misclassifications of ECG signals. For example, in multichannel embodiments such as a multichannel arrangement of electrodes shown in FIG. 3, the amplitudes of some channels may be different from other channels. A patient 110 wearing the multichannel device with low-amplitude QRS complexes may be above the threshold 424 on some channels but below the threshold 424 on other channels. In such embodiments, a patient 110 can be determined to as asystolic only if the peak-to-peak amplitudes of the QRS complexes on all channels are below the threshold amplitude. Otherwise, in some examples the patient can be determined to have fine VF.

In some embodiments, the threshold 424 can be adjustable for each patient 110. For example, the threshold 424 can be selected when the patient 110 is fitted with a garment type support structure 112. The patient 110 is known to not be asystolic at that time, so a threshold could be chosen that is a fraction of the peak-to-peak QRS amplitude for each channel, for example the threshold 424 can be set as 25% of the peak-to peak amplitude of normal QRS complexes for each channel. Thus, some channels can have thresholds 424 below 100 μV, while other channels may have higher thresholds 424. In some embodiments, the WCD system 100 can be configured with a maximum asystole threshold, for example 200 μV in some embodiments, regardless of the patient's actual QRS amplitude. In some embodiments, during the fitting process the patient 110 can be asked to lie down while the QRS amplitudes are measured, since a patient experiencing asystole may be unconscious and lying down, with the thresholds 424 being selected using these QRS amplitude measurements.

It should be noted that QRS amplitudes can vary with patient posture. QRS amplitudes have been seen that can vary by about 50% over time on a single vector in normal, healthy patients. As a result, in some embodiments the asystole threshold 424 can be set so that it is low enough to avoid being crossed by the normal QRS amplitude variations. In some embodiments, the thresholds 424 can be set for different patient postures. In a further embodiment, the WCD system may include a sensor for determining the patient's posture, with the threshold 424 being dynamically adjusted based on the determined posture. For example, patient posture may be detected as disclosed in U.S. patent application Ser. No. 15/863,551 entitled "WEARABLE CARDIOVERTER DEFIBRILLATOR HAVING ADJUSTABLE ALARM TIME" filed on Jan. 5, 2018, which is incorporated by reference in its entirety for all purposes.

In some embodiments, the asystole threshold 424 can be adjusted during the normal wear time by the patient 110. For example, if a patient 110 receives an asystole alert and presses the alert/stop/response button 120 which is used in WCD system 100 to indicate the patient 110 is conscious and thus should not be shocked, the WCD system can configured to take this stop button 120 actuation as an indication that the patient 110 is not in asystole and that the asystole thresholds 424 should be adjusted accordingly.

Referring now to FIG. 5, a diagram of ECG signals illustrating p-waves in addition to QRS complexes wherein P-wave morphologies are accounted for in detected asystole in accordance with one or more embodiments will be discussed. In the case of patients with sudden complete heart block it is possible for the patient 110 to have p-waves but no QRS complexes. The p-waves, however, may be greater in amplitude than the asystole threshold 424 so the p-waves can be mistaken as QRS complexes, which may prevent asystole detection. Furthermore, p-waves can continue at the patient's normal heart rate for a period of time, so heart block cannot be detected using heart rate alone. In accordance with one or more embodiments, complete heart block patients are classified as asystolic because complete heart block has no QRS complexes and is non-perfusing.

In some embodiments, WCD system 100 can be configured to detect complete heart block. For example, the WCD system 100 can capture the patient's normal QRS amplitude, for example during fitting, and can monitors the patient's QRS complexes for a sudden shift to a lower amplitude. A sudden change or drop to a lower QRS amplitude may be indicative of complete heart block. As shown in plot 500, an ECG signal 510 can have normal QRS complexes 512 with normal p-waves as shown. ECG signal 510 omits t-waves for purposes of discussion. P-waves are normally in the range of about 100 μV to about 200 uV while QRS complexes are normally 500 μV to about 3.0 mV in amplitude. In some embodiments, a sudden drop in the amplitude of detected complexes of greater than 50% with an amplitude less than about 200 μV can be determined to be indicative of complete heart block. Thus, in some embodiments, the peak-to-peak amplitude values of the QRS complexes 512 can be measured and monitored, and complete heart block can be detected when the peak-to-peak amplitudes are less than 50% of their normal values and/or when the amplitudes are less than about 200 μV.

In some embodiments a template can be used by WCD system 100 for detecting complete heart block. For example, a QRS complex template 520 can be created during the patient's normal rhythm and stored in a memory of the WCD system 100. In other embodiments, a p-wave template 522 can be created and stored in a memory of the WCD system 100. In such embodiments, the WCD system 100 can be configured to compare detected QRS complexes to the QRS complex template 520 and/or compare detected p-waves to the p-wave template 522. The detected morphology of the p-waves during complete heart block should be dramatically different than a normal p-wave as reflected by the p-wave template 522.

Plot 502 shows an ECG signal 514 showing a normal QRS complex 512 with a normal p-wave, a low-amplitude QRS complex 516 with a normal p-wave, and the absence of a QRS complex 520 with an abnormal p-wave 518. Plot 504 shows the ECG signal 514, with the low-amplitude QRS complex 516 compared with the QRS complex template 520. Plot 504 also shows an abnormal p-wave 518 such as might occur during asystole which is compared with a normal p-wave template 522. Various techniques can be employed to compare a received QRS complex with a QRS complex template 520 and/or to compare a receive p-wave with a p-wave template 522. For example, pattern matching techniques can be used, correlation techniques such as a cross-correlation or an auto-correlation wherein a high correlation value can indicate a match between the received signal and the template, and a low correlation value can indicate a sufficient change to indicate either fine VF for the QRS complex, or to indicate asystole for the p-wave, and so on.

Figure 6:
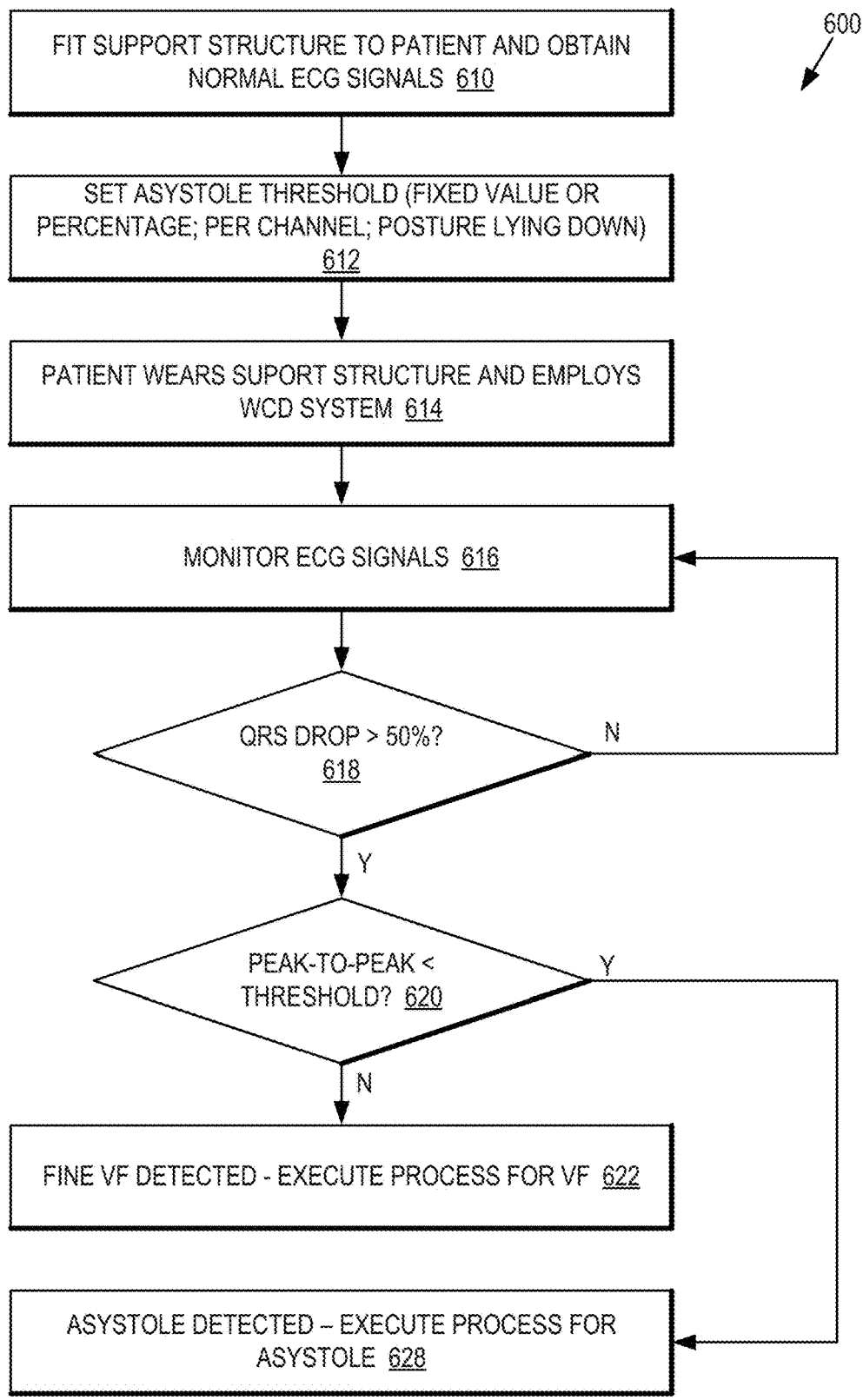
FIG. 6 is a diagram of a method to detect asystole in a patient and to discriminate asystole from fine ventricular fibrillation (VF) in accordance with one or more embodiments.
Figure 13:
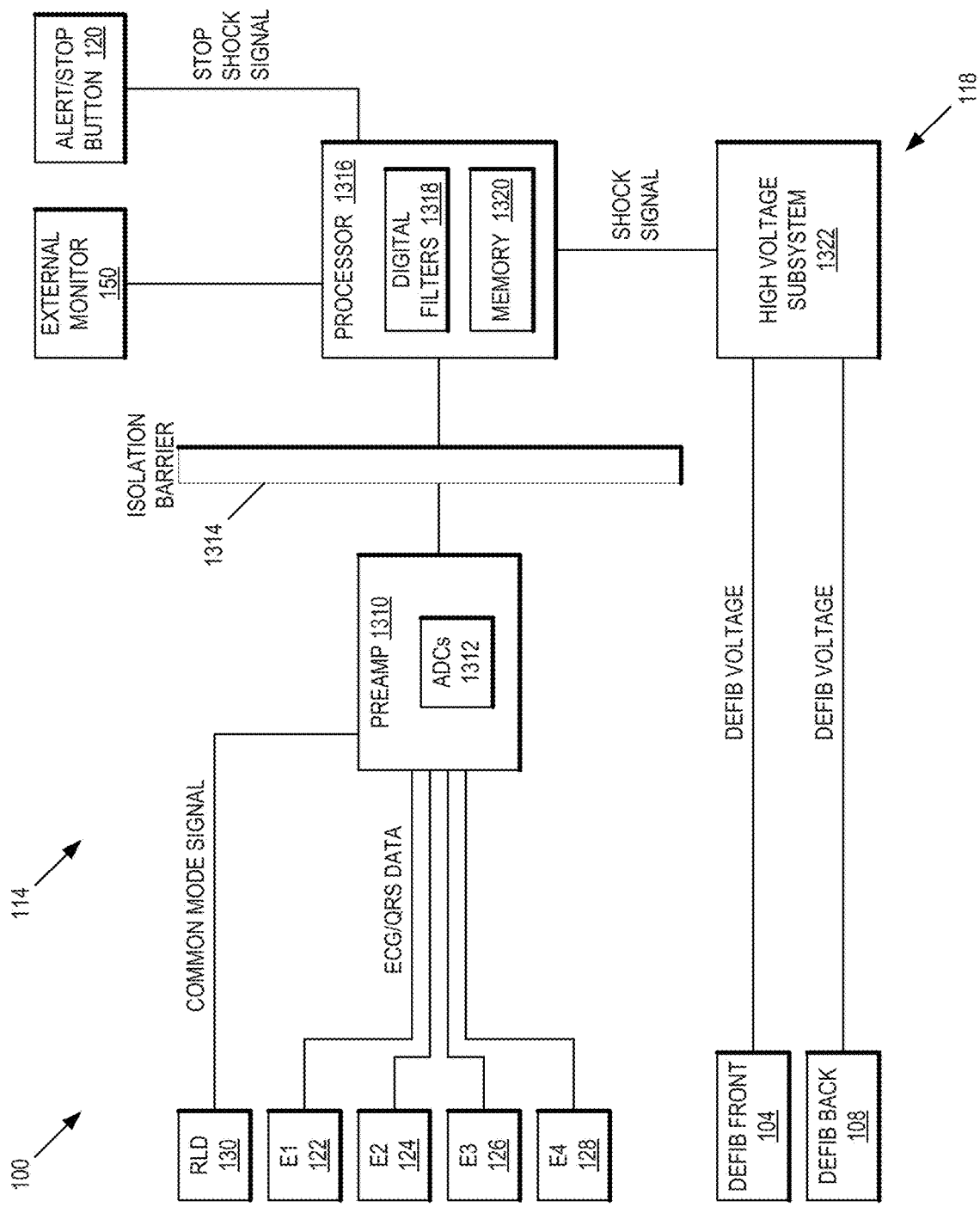
FIG. 13 is a diagram of the elements of a wearable cardioverter defibrillator (WCD) using an external monitor to provide additional patient physiological parameter information to the WCD in accordance with one or more embodiments.

Referring now to FIG. 6, a diagram of a method to detect asystole in a patient and to discriminate asystole from fine ventricular fibrillation (VF) in accordance with one or more embodiments will be discussed. Although FIG. 6 shows one particular order and number of operations of method 600, it should be noted that method 600 can encompass various other orders of the operations and/or can include more or fewer operations than shown, and the scope of the disclosed subject matter is not limited in these respects. Method 600 can be implemented by a processor of WCD system 100, for example by processor 1316 as shown in FIG. 13 below, and can be realized a machine readable instructions that when executed result in the operations shown in FIG. 6. Such instructions can be stored in a storage device or memory of WCD system 100, such as memory 1320 of FIG. 13 below. Some of the operations of method 600 can be performed in whole or in part by WCD 100, some of the operations of method 600 can be performed in whole or in part by another device such as by external monitor 150 of FIG. 1, and/or some of the operations of method 600 can be performed in whole or in part by the patient 110 or by a bystander or some other person such as medical practitioner, and so on.

At operation 610, support structure 112 can be fit to patient 110 at an initial fitting, for example fitting a vest style support structure 112 as shown in FIG. 2 and FIG. 3 to patient 110, and normal ECG signals can be obtained during the fitting. At operation 612, one or more asystole thresholds 424 can be set during the fitting. The asystole thresholds can be set to a fixed value, or set to a percentage of the peak-to-peak value 414 of a normal ECG signal. In some examples, each ECG channel can have its own unique asystole threshold 424. In some examples, the normal ECG signals can be obtained when the patient 110 being fitted is lying down or in some similar posture that would be expected during asystole, and the asystole thresholds can be set accordingly. At operation 614, the patient 110 wears support structure 112 and employs WCS system 100 to monitor the patient's ECG signals at operation 616 and optionally any other patient physiological parameter as desired or needed. Such monitoring at operation 616 can include monitoring and measuring the peak-to-peak amplitudes 414 of the patient's QRS complexes.

Figure 12:
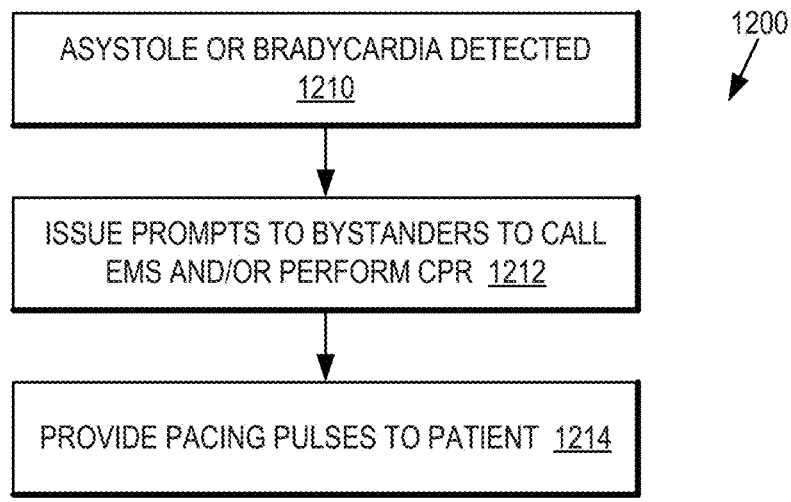
FIG. 12 is a method to address asystole or bradycardia in a patient using a wearable cardioverter defibrillator (WCD) in accordance with one or more embodiments.

A determination can be made at operation 618 when the patient's QRS peak-to-peak amplitudes 414 drop by greater than 50% or some predetermined amount. If the QRS amplitudes have not dropped sufficiently, then ECG signals may be continued to be monitored at operation 616. When the QR amplitudes have dropped by the predetermined amount, a determination can be made at operation 620 whether the peak-to-peak values 414 are less than the asystole threshold 424. If the peak-to-peak values 414 are not less than the asystole threshold 424, then it can be determined at operation 622 that fine VF has been detected, and a process for VF or fine VF can be executed, for example an analysis as to whether a therapeutic shock 111 should be delivered to the patient 110. When the peak-to-peak values 414 are determined at operation 620 to be less than the asystole threshold 424, then it can be determined at operation 628 that asystole has been detected, and a process for asystole can be executed, for example method 1200 as shown in FIG. 12 and as discussed below can be executed.

Figure 7:
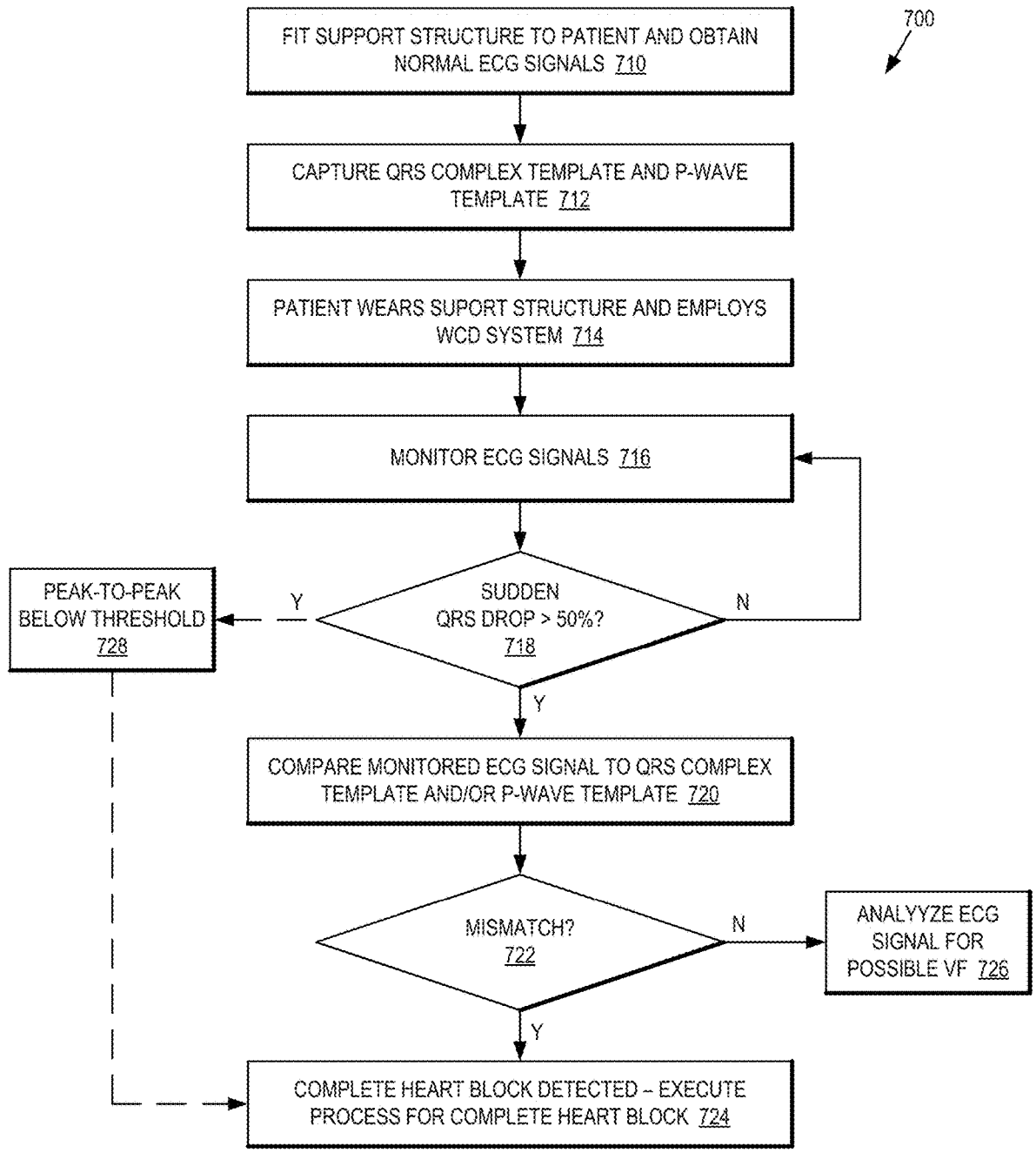
FIG. 7 is a diagram of a method to detect complete heart block in a patient in accordance with one or more embodiments.

Referring now to FIG. 7, a diagram of a method to detect complete heart block in a patient in accordance with one or more embodiments will be discussed. Although FIG. 7 shows one particular order and number of operations of method 700, it should be noted that method 700 can encompass various other orders of the operations and/or can include more or fewer operations than shown, and the scope of the disclosed subject matter is not limited in these respects. Method 700 can be implemented by a processor of WCD system 100, for example by processor 1316 as shown in FIG. 13 below, and can be realized a machine readable instructions that when executed result in the operations shown in FIG. 7. Such instructions can be stored in a storage device or memory of WCD system 100, such as memory 1320 of FIG. 13 below. Some of the operations of method 700 can be performed in whole or in part by WCD 100, some of the operations of method 700 can be performed in whole or in part by another device such as by external monitor 150 of FIG. 1, and/or some of the operations of method 700 can be performed in whole or in part by the patient 110 or by a bystander or some other person such as medical practitioner, and so on.

At operation 710, support structure 112 can be fit to patient 110 at an initial fitting, for example fitting a vest style support structure 112 as shown in FIG. 2 and FIG. 3 to patient 110, and normal ECG signals can be obtained during the fitting. At operation 712, a QRS complex template 520 can be captured and/or a p-wave template 522 can be captured. As with the setting of the asystole thresholds in method 600 above, the templates can be captured when the patient 110 is in a selected postures such as lying down or in a prone position. At operation 714, the patient 110 wears support structure 112 and employs WCS system 100 to monitor the patient's ECG signals at operation 616 and optionally any other patient physiological parameter as desired or needed. Such monitoring at operation 716 can include monitoring and measuring the peak-to-peak amplitudes 414 of the patient's QRS complexes.

A determination can be made at operation 718 when the patient's QRS peak-to-peak amplitudes 414 drop by greater than 50% or some predetermined amount. If the QRS amplitudes have not dropped sufficiently, then ECG signals may be continued to be monitored at operation 716. In one option, with a sudden drop in the QRS amplitude, and the QRS amplitudes are measured at operation 728 to be below the asystole threshold 424, then complete heart block can be detected, and operation 724 can be executed as will be discussed in further detail below. In another option, with a sudden drop in the QRS amplitude, the monitored ECG signal can be compared at operation 720 to the QRS complex template 520 and/or the p-wave template 522. A determination can be made at operation 722 whether there is a sufficient mismatch between the monitored ECG signal and the QRS complex template 520 and/or the p-wave template 522. If there is not a sufficient mismatch, then then the monitored ECG signal can be analyzed for possible VF at operation 726. When operation 722 determines there is a sufficient mismatch between the monitored ECG signal and the QRS complex template 520 and/or the p-wave template 522, complete heat block can be detected at operation 728, a process for complete hear block can be executed, for example method 1200 of FIG. 12 as discussed below can be executed.

Figure 8:
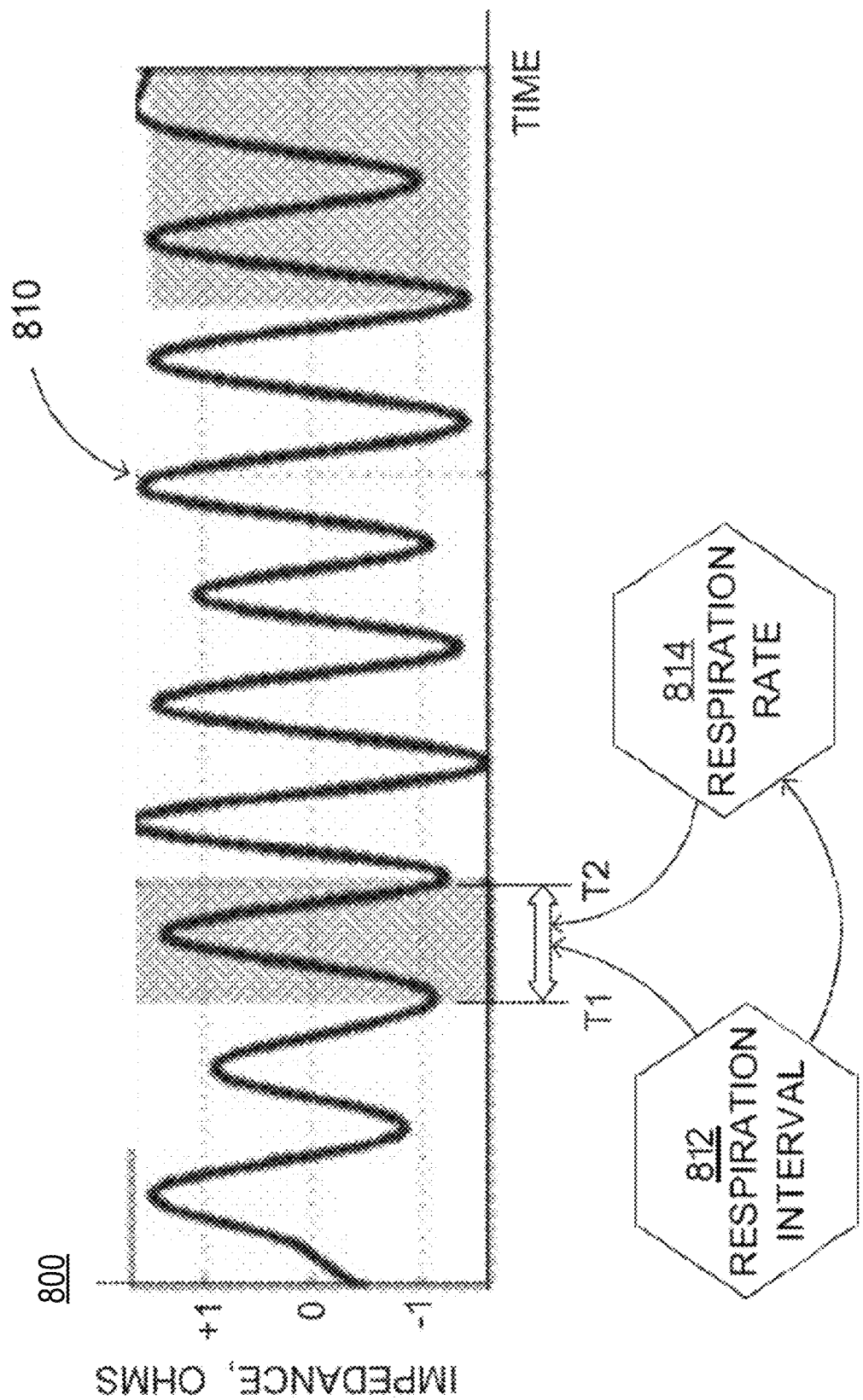
FIG. 8 is a diagram illustrating measurement of a respiration rate of a patient in accordance with one or more embodiments.

Referring now to FIG. 8, a diagram illustrating measurement of a respiration rate of a patient in accordance with one or more embodiments will be discussed. In the event the ECG signal obtained with WCD system 100 appears to show asystole, for example with peak-to-peak amplitude is near or below the threshold 424, then WCD system 100 can check to see if the patient 110 is breathing before rendering a final decision that the patient 110 is in asystole. In some embodiments, patient respirations can be detected such as disclosed in U.S. Published Patent Application No. 20180117299 entitled "WEARABLE CARDIOVERTER DEFIBRILLATOR (WCD) SYSTEM MEASURING PATIENT'S RESPIRATION", filed on Oct. 25, 2017. In other embodiments, respirations can be detected using the DC level as described in U.S. Provisional Patent Application 62/911,024 filed Oct. 4, 2019 entitled "DC RESPIRATION RATE DETECTOR". Still other embodiments may use other techniques to detect patient respiration. In some embodiments, WCD system 100 may be configured to measure impedance values between two ECG electrodes contacting the patient's skin. Plot 800 shows detected patient impedance values 810 versus time. The impedance values 810 will vary by about +/−1 or 2 ohms as the patient breathes. The time between consecutive minimum values time T1 and time T2 can be referred to as the respiration interval 812 from which the respiration rate 814 can be calculated.

In some embodiments, WCD system 110 can include a motion sensor, for example an accelerometer and/or light emitting devices to sense motion of the patient. These sensors can enhance respiration detection performance because an impedance-based respiration detector potential can very motion sensitive. WCD patients are ambulatory, so movement of the patient is common. Patients who are non-perfusing, however, will typically not be moving, at least under their own volition, so it can be assumed that if the patient 110 is moving, as evidenced or by an accelerometer or other motion detector,) then the patient 110 must be breathing.

It should be noted that different patients can tolerate low heart rates to different degrees. Some patients may lose consciousness at 40 beats per minute (BPM) whereas other patients may not lose consciousness until their heart rates fall to 20 BPM. Previous WCDs typically used fixed rate threshold for detecting bradycardia. This approach, however, may cause unnecessary bradycardia alarms in some patients but also may fail to alarm for some non-perfusing rhythms. To address this variation of the effect of bradycardia on different patients, patient respiration may be used in conjunction with heart rate to detect whether the patient 110 is experiencing bradycardia.

Figure 9:
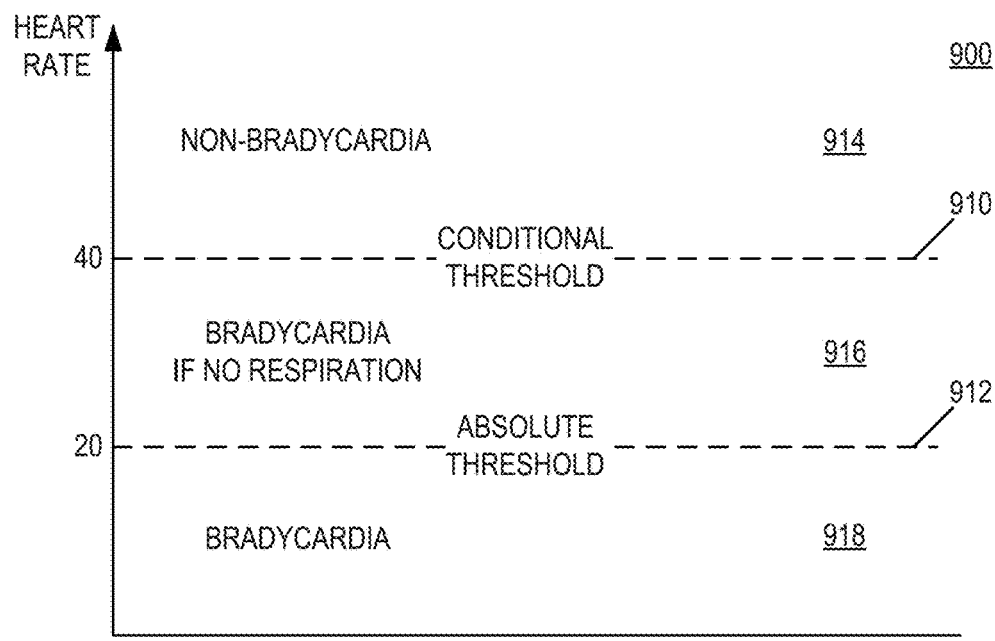
FIG. 9 is a diagram of detection of bradycardia in a patient using a conditional heart rate zone in combination with patient respiration in accordance with one or more embodiments.

Referring now to FIG. 9, a diagram of detection of bradycardia in a patient using a conditional heart rate zone in combination with patient respiration in accordance with one or more embodiments will be discussed. As shown in FIG. 9, respiration detection can be used in determining whether bradycardia is perfusing or non-perfusing. Chart 900 shows patient heart rates in beats per minute (BPM). A conditional threshold 910 can be set at a first heart rate, for example 40 BPM. An absolute threshold 912 can be set at a second heart rate, for example 20 BPM. Heart rates above the conditional threshold 910 can be considered to be in the non-bradycardia zone 914 such that patient 110 is not experiencing bradycardia. Heart rates below the absolute threshold 912 can be considered to be in the bradycardia zone 918. Heart rates below the conditional threshold 910 but above the absolute threshold 912 can be considered to be the conditional heart rate zone 916. Heart rates in the conditional heart rate zone 916 will not trigger a bradycardia alarm if patient respiration is detected. If no respiration is detected in the conditional heart rate zone 918, then a bradycardia alarm will be triggered. When the patient's heart rate falls below the absolute threshold, then the bradycardia alarm will be triggered regardless of the presence or absence of patient respirations.

Figure 10:
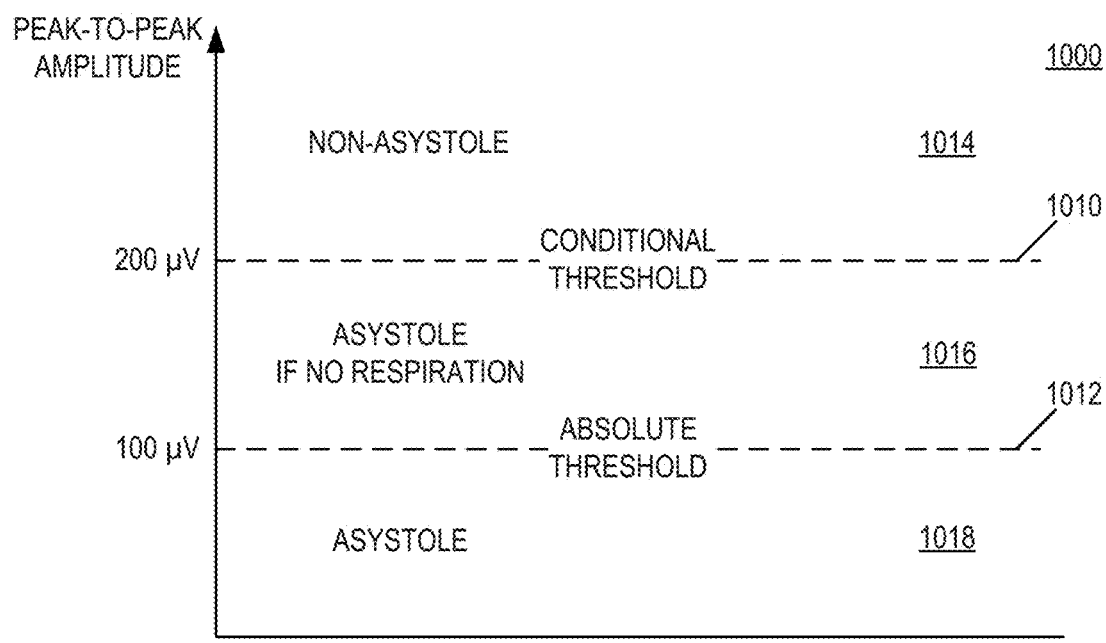
FIG. 10 is a diagram of detection of asystole in a patient using a conditional amplitude zone in combination with patient respiration in accordance with one or more embodiments.

Referring now to FIG. 10, a diagram of detection of asystole in a patient using a conditional amplitude zone in combination with patient respiration in accordance with one or more embodiments will be discussed. As shown in FIG. 10, respiration detection can also be useful in detecting complete heart block. In some embodiments, this is in addition to detection of bradycardia, for example as discussed with respect to FIG. 9, above. While bradycardia detection can use a conditional heart rate threshold, in some embodiments asystole detection can utilize a conditional amplitude threshold. For example, chart 900 shows peak-to-peak QRS complex amplitude in volts. A conditional threshold 1010 can be set at a first amplitude, for example 200 µV. An absolute threshold 1012 can be set at a second amplitude, for example 100 µV. Signals having amplitudes above the conditional threshold 1010 can be considered to be in the non-asystole zone 1014 such that patient 110 is not experiencing asystole. Signals having amplitudes below the absolute threshold 1012 can be considered to be in the asystole zone 1018 and definitely classified as asystole. Signals having amplitudes below the conditional threshold 1010 but above the absolute threshold 1012 can be considered to be the conditional amplitude zone 1016. Signal amplitudes in the conditional amplitude zone 1016 will not trigger an asystole alarm if patient respiration is detected. If no respiration is detected in the conditional amplitude zone 918, then an asystole alarm will be triggered. When the patient's amplitude falls below the absolute threshold, then the asystole alarm will be triggered regardless of the presence or absence of patient respirations.

Such an arrangement of using respiration in combination with signal amplitude can assist with detection of complete heart block because p-waves would tend to fall in the conditional amplitude zone 016. Thus, when asystole occurs where there is no QRS complex but a p-wave may still be present, the amplitude of the p-wave can be in the conditional amplitude zone 1016. In this situation, the absence of patient respiration can confirm asystole.

Figure 11:
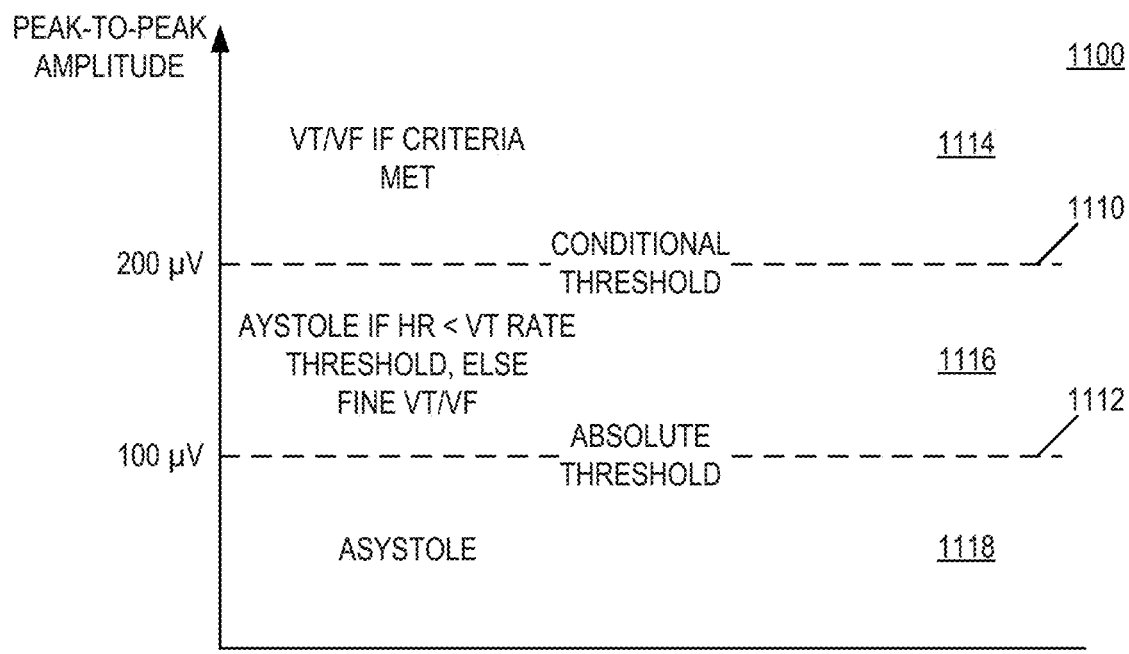
FIG. 11 is a diagram of discrimination between asystole and fine ventricular tachycardia (VT) or ventricular fibrillation (VF) using a conditional amplitude zone in accordance with one or more embodiments.

Referring now to FIG. 11, a diagram of discrimination between asystole and fine ventricular tachycardia (VT) or ventricular fibrillation (VF) using a conditional amplitude zone in accordance with one or more embodiments will be discussed. Chart 1100 shows a conditional amplitude threshold 1110, an absolute amplitude threshold 1112, and a conditional amplitude zone 1116 for peak-to-peak QRS complex signals similar to that shown in FIG. 10. Within conditional amplitude zone 1116, other factors may be used to distinguish fine VF from complete heart block. In some embodiments, the patient's heart rate and QRS complex width can be used to detect VT or VF as described in U.S. Pat. No. 10,105,547 entitled "WEARABLE CARDIOVERTER DEFIBRILLATOR (WCD) CAUSING PATIENT'S QRS WIDTH TO BE PLOTTED AGAINST THE HEART RATE". In such embodiments, rhythms can be classified as VT/F in zone 1114 when VT/VF criteria are met, and a detected rhythm that meets the VT/VF criteria and falls in the conditional amplitude zone 1116 can be classified as fine VT/VF. If the heart rate falls below the VT rate threshold, however, and the amplitude is in the conditional amplitude zone 1116, then such rhythms in the conditional amplitude zone would be classified as asystole. In any event, amplitudes below absolute threshold 1112 in asystole zone 1118 will be classified as asystole.

Referring now to FIG. 12, a method to address asystole or bradycardia in a patient using a wearable cardioverter defibrillator (WCD) in accordance with one or more embodiments will be discussed. Patients experiencing asystole or severe bradycardia may quickly lose consciousness and may die if prompt treatment is not provided. Method 1200 may be executed when asystole or bradycardia conditions are met. Asystole or bradycardia can be detected at operation 1210. To help the patient 110, WCD system 100 can issue prompts at operation 1212 to any bystander to call EMS and/or to provide CPR until help arrives. For example, the system may be configured to issue voice prompts to bystanders to intervene as described in U.S. Pat. No. 10,426,964 entitled "WEARABLE CARDIAC DEFIBRILLATOR SYSTEM EMITTING CPR PROMPTS FOR BYSTANDER". In other embodiments, WCD 100 can be configured to optionally provide temporary external pacing to patient 110 at operation 1214 similar to that described in U.S. Pat. No. 8,838,236 entitled "WEARABLE CARDIAC DEFIBRILLATOR SYSTEM WITH ANTI-BRADYARRHYTHMIA PACING & METHODS" to bridge the patient over until EMS arrives.

Referring now to FIG. 13, a diagram of the elements of a wearable cardioverter defibrillator (WCD) using an external monitor to provide additional patient physiological parameter information to the WCD in accordance with one or more embodiments will be discussed. The WCD 100 shown in FIG. 13 incorporates one or more of the features discussed herein to detect asystole and/or bradycardia. In some embodiments, WCD system 100 can include an external monitor 150 that can comprise pulse sensor or non-invasive blood pressure measurement capability. WCD system 100 can be configured to also use the data from one or more of these sensors to determine if the patient 110 is perfusing.

The ECG electrodes, (E1) 122, (E2) 124, (E3) 126, and (E4) 128, can comprise silver or silver plated copper electrodes that "dry" attach to the skin of the patient 110. The ECG electrodes provide ECG/QRS data to preamplifier 1310 in hub/monitoring device 114. The preamplifier 132 may have a wide dynamic range at its input, for example +/−1.1 V which is much larger than the amplitude of the ECG signals which are about 1 mV. The preamplifier 1310 includes analog-to-digital converters (ADCs) 1312 to convert the ECG signals into a digital format. A right-leg drive (RLD) electrode 130 can be used to provide a common mode signal so that the ECG signal from the ECG electrodes can be provided to preamplifier 1310 as differential signals. The digital ECG signals are provided from the preamplifier 1310 eventually to the main processor 1316 of monitor 150 via an isolation barrier 1314 which operates to electrically isolate the preamplifier 1310 and the ECG signals from the rest of the circuitry of WCD 100.

The processor 1316 processes the digital ECG/QRS data received from the preamplifier 1310 with one or more digital filters 1318. Since the preamplifier 1312 has a wide dynamic range that is much wider than the amplitude range of the ECG signals, digital filters 1318 be utilized to process the ECG/QRS data without concern for clipping the incoming signals. One of the digital filters 1318 can include a matched filter to facilitate identification of QRS pulses in the incoming data stream. The wide dynamic range of the preamplifier 1310 allows at least most of the ECG filtering to happen in software without the signal being clipped. Digital filters 1318 can be very effective at removing artifacts from the ECG/QRS data and may contribute to the enhanced false positive performance, that is a lower false positive rate, of the WCD 100 according to embodiments as described herein.

The processor 1318 can apply the rhythm analysis algorithm (RAA) stored in memory 1320 using QRS width information and heart rate data extracted from the digital ECG data using segment-based processing analysis and/or QRS width versus heart rate 7 to make a shock or no-shock determination for VT and/or VF. The RAA receives the digitized ECG signal and calculates the heart rate and QRS width for each segment. The digitized ECG signal is passed over the isolation barrier 1314, and the heart rate is derived from the digitized ECG signal. The heart rate and QRS width are used for making a shock/no-shock decision for each segment, which then can lead to an alarm and a shock. In the event a shockable event is identified, the processor 1316 will open a tachycardia episode to start the shock process. Unless the patient 110 provides a patient response using the alert/stop button 120 or other user interface to send a stop shock signal to the processor 1316 to intervene before the shock is applied, the processor 1318 can send a shock signal to the high voltage subsystem 1322 in the carry pack/defibrillator 118 which will apply a defibrillation voltage across the defib front electrode 104 and the defib back electrode 108 to apply one or more therapeutic shocks until there is no longer any shockable event (VT or VF) or until the energy in the high voltage subsystem 1322 is depleted.

Although the claimed subject matter has been described with a certain degree of particularity, it should be recognized that elements thereof may be altered by persons skilled in the art without departing from the spirit and/or scope of claimed subject matter. It is believed that the subject matter pertaining to asystole and complete heart block detection and many of its attendant utilities will be understood by the forgoing description, and it will be apparent that various changes may be made in the form, construction and/or arrangement of the components thereof without departing from the scope and/or spirit of the claimed subject matter or without sacrificing all of its material advantages, the form herein before described being merely an explanatory embodiment thereof, and/or further without providing substantial change thereto. It is the intention of the claims to encompass and/or include such changes.

What is claimed is:

1. An apparatus of a wearable cardioverter defibrillator (WCD) system, comprising:
    a support structure wearable by a patient;
    a plurality of electrocardiogram (ECG) electrodes capable of being applied to the skin of the patient to obtain an ECG signal;
    a processor to receive and analyze the ECG signal of the patient, wherein the processor is configured to monitor four or more channels of the ECG signal; and
    a high voltage subsystem coupled with defibrillation electrodes configured to be coupled with patient, wherein the processor is configured to cause the high voltage subsystem to apply a therapeutic shock to the patient through the defibrillation electrodes in response to a shockable event detected by the processor from the ECG signal;
    wherein the processor is further configured to:
    measure a peak-to-peak amplitude of QRS complexes of the ECG signal; and
    detecting asystole in the patient when the peak-to-peak amplitude of one or more QRS complexes is less than an asystole threshold; and
    wherein a unique asystole threshold is set for each of the four or more channels.

2. The apparatus of claim 1, wherein the unique asystole threshold of at least one of the four or more channels is set to a fixed value.

3. The apparatus of claim 2, wherein the fixed value ranges from about 100 microvolts to about 200 microvolts.

4. The apparatus of claim 1, wherein the unique asystole threshold of at least one of the four or more channels is set to a percentage of a peak-to-peak amplitude of a normal QRS complex of the patient.

5. The apparatus of claim 1, wherein the processor is further configured to:
    detect respiration of the patient; and
    determine that the patient is in asystole when the peak-to-peak amplitude of one or more of the QRS complexes is lower than a unique conditional threshold and higher than an absolute threshold for at least one of the four or more channels, and when no patient respiration is detected.

6. The apparatus of claim 1, wherein asystole is detected only when the peak-to-peak amplitudes of QRS complexes in all four channels falls below the unique asystole threshold for each of the four or more channels.

7. An apparatus of a wearable cardioverter defibrillator (WCD) system, comprising:
    a support structure wearable by a patient;
    a plurality of electrocardiogram (ECG) electrodes capable of being applied to the skin of the patient to obtain an ECG signal;
    a processor to receive and analyze the ECG signal of the patient, wherein the processor is configured to monitor four or more channels of the ECG signal; and
    a high voltage subsystem coupled with defibrillation electrodes configured to be coupled with patient, wherein the processor is configured to cause the high voltage subsystem to apply a therapeutic shock to the patient through the defibrillation electrodes in response to a shockable event detected by the processor from the ECG signal;
    wherein the processor is further configured to:
    measure a peak-to-peak amplitude of QRS complexes of the ECG signal;
    detect respiration of the patient; and
    detect asystole in the patient when the peak-to-peak amplitude of one or more of the QRS complexes is lower than a conditional asystole threshold and higher than an absolute asystole threshold, and when no patient respiration is detected.

8. The apparatus of claim 7, wherein the conditional asystole threshold is set to a fixed value.

9. The apparatus of claim 8, wherein the fixed value ranges from about 100 microvolts to about 200 microvolts.

10. The apparatus of claim 7, wherein the conditional asystole threshold is set to a percentage of a peak-to-peak amplitude of a normal QRS complex of the patient.

11. The apparatus of claim 7, wherein a unique conditional asystole threshold is set for each of the four or more channels.

12. The apparatus of claim 7, wherein asystole is detected only when the peak-to-peak amplitudes of QRS complexes in each of the four or more of the channels falls below the conditional asystole threshold.

13. An apparatus of a wearable cardioverter defibrillator (WCD) system, comprising:
    a support structure wearable by a patient;
    a plurality of electrocardiogram (ECG) electrodes capable of being applied to the skin of the patient to obtain an ECG signal;
    a processor to receive and analyze the ECG signal of the patient, wherein the processor is configured to monitor four or more channels of the ECG signal; and
    a high voltage subsystem coupled with defibrillation electrodes configured to be coupled with patient, wherein the processor is configured to cause the high voltage subsystem to apply a therapeutic shock to the patient through the defibrillation electrodes in response to a shockable event detected by the processor from the ECG signal;
    wherein the processor is further configured to:
    measure a peak-to-peak amplitude of QRS complexes of the ECG signal; and
    detecting asystole in the patient when the peak-to-peak amplitude of one or more QRS complexes is less than an asystole threshold; and
    wherein asystole is detected only when the peak-to-peak amplitudes of QRS complexes in each of the four or more channels falls below the asystole threshold.

14. The apparatus of claim 13, wherein the asystole threshold is set to a fixed value.

15. The apparatus of claim 14, wherein the fixed value ranges from about 100 microvolts to about 200 microvolts.

16. The apparatus of claim 13, wherein the asystole threshold is set to a percentage of a peak-to-peak amplitude of a normal QRS complex of the patient.

17. The apparatus of claim 13, wherein a unique asystole threshold is set for each of the four or more channels.

18. The apparatus of claim 13, wherein the processor is further configured to:
    detect respiration of the patient; and
    determine that the patient is in asystole when the peak-to-peak amplitude of one or more of the QRS complexes is lower than a conditional systole threshold and higher than an absolute asystole threshold, and when no patient respiration is detected.

* * * * *